United States Patent
Riegel et al.

(10) Patent No.: US 7,947,771 B2
(45) Date of Patent: May 24, 2011

(54) INSOLUBLE METAL SULFATES IN WATER ABSORBING POLYMERIC PARTICLES

(75) Inventors: Ulrich Riegel, Landstuhl (DE); Thomas Daniel, Waldsee (DE); Dieter Hermeling, Böhl-Iggelheim (DE); Mark Elliott, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 551 days.

(21) Appl. No.: 11/667,898

(22) PCT Filed: Nov. 28, 2005

(86) PCT No.: PCT/EP2005/012679
§ 371 (c)(1),
(2), (4) Date: May 16, 2007

(87) PCT Pub. No.: WO2006/058683
PCT Pub. Date: Jun. 8, 2006

(65) Prior Publication Data
US 2007/0293617 A1    Dec. 20, 2007

(30) Foreign Application Priority Data
Nov. 30, 2004   (DE) .................. 10 2004 057 868

(51) Int. Cl.
*C08K 3/30* (2006.01)
*C08L 31/02* (2006.01)
*C08L 31/00* (2006.01)
*C08L 33/00* (2006.01)
*C08L 33/02* (2006.01)
*C08F 220/06* (2006.01)

(52) U.S. Cl. ........ 524/423; 524/436; 524/543; 524/556; 524/559

(58) Field of Classification Search .............. 524/423, 524/436, 543, 556, 559
See application file for complete search history.

(56) References Cited

U.S. PATENT DOCUMENTS

| 5,019,606 | A | 5/1991 | Marten et al. |
| 5,331,059 | A | 7/1994 | Engelhardt et al. |
| 5,489,469 | A * | 2/1996 | Kobayashi et al. ........... 442/393 |
| 6,472,478 | B1 | 10/2002 | Funk et al. |
| 6,503,979 | B1 | 1/2003 | Funk et al. |
| 6,559,239 | B1 | 5/2003 | Riegel et al. |
| 6,605,673 | B1 * | 8/2003 | Mertens et al. ............ 525/329.5 |
| 6,657,015 | B1 | 12/2003 | Riegel et al. |
| 6,831,122 | B2 | 12/2004 | Daniel et al. |
| 7,183,360 | B2 | 2/2007 | Daniel et al. |
| 2004/0019342 | A1 * | 1/2004 | Nagasuna et al. ....... 604/385.01 |
| 2006/0211828 | A1 | 9/2006 | Daniel et al. |

FOREIGN PATENT DOCUMENTS

| DE | 4214334 | 11/1993 |
| DE | 19807992 | 7/1999 |
| DE | 19807502 | 9/1999 |
| DE | 19854573 | 5/2000 |
| DE | 19854574 | 5/2000 |
| DE | 10334584 | 2/2005 |
| DE | 102004015686 | 10/2005 |
| EP | 0083022 | 7/1983 |
| EP | 0349935 | 1/1990 |
| EP | 0530438 | 3/1993 |
| EP | 0543303 | 5/1993 |
| EP | 0621041 | 10/1994 |
| EP | 1457541 | 9/2004 |
| WO | WO-02/060983 | 8/2002 |
| WO | WO-03/031482 | 4/2003 |
| WO | WO-2004/011048 | 2/2004 |

OTHER PUBLICATIONS

International Search Report in PCT/EP2005/012679 dated Oct. 27, 2006.

* cited by examiner

*Primary Examiner* — Vasu Jagannathan
*Assistant Examiner* — Karuna P Reddy
(74) *Attorney, Agent, or Firm* — Marshall, Gerstein & Borun LLP

(57) ABSTRACT

The invention concerns water-absorbing polymeric particles possessing high saline flow conductivity in the swollen state which comprise insoluble metal sulfates as synergistic fillers, and also a process for their production and their use.

13 Claims, No Drawings

INSOLUBLE METAL SULFATES IN WATER ABSORBING POLYMERIC PARTICLES

CROSS-REFERENCE TO RELATED APPLICATIONS

This is the U.S. national phase application of International Application No. PCT/EP2005/012679, filed Nov. 28, 2005, which claims the benefit of German patent application No. 10 2004 057 868.0, filed Nov. 30, 2004.

The present invention relates to water-absorbing polymeric particles comprising insoluble metal sulfates and also to a process for producing them and to their use.

Water-absorbing polymers are in particular polymers of (co)polymerized hydrophilic monomers, graft (co)polymers of one or more hydrophilic monomers on a suitable grafting base, crosslinked ethers of cellulose or of starch, crosslinked carboxymethylcellulose, partially crosslinked polyalkylene oxide or natural products swellable in aqueous fluids, such as guar derivatives for example. Such hydrogels are used as products capable of absorbing aqueous solutions to manufacture diapers, tampons, sanitary napkins and other hygiene articles, but also as water-retaining agents in market gardening.

To improve their performance characteristics, such as saline flow conductivity (SFC) in the diaper and absorbency under load (AUL), water-absorbing polymers are generally surface or gel postcrosslinked. This postcrosslinking preferably takes place in the aqueous gel phase or as postcrosslinking of ground and classified polymeric particles.

Postcrosslinking is to be understood as referring to the gel or secondary crosslinking of water-absorbing hydrogels.

Useful crosslinkers for this purpose are compounds comprising two or more groups capable of forming covalent bonds with the carboxylate groups of the hydrophilic polymer. Examples of suitable compounds are di- or polyglycidyl compounds, such as diglycidyl phosphonates, alkoxysilyl compounds, polyaziridines, polyamines or polyamidoamines, and the identified compounds can also be used in mixtures with each or one another (see for example EP-A 083 022, EP-A 543303 and EP-A 530 438). Polyamidoamines suitable for use as crosslinkers are described in EP-A 349 935 in particular.

Furthermore, compounds described as suitable crosslinkers include 2-oxazolidone and its derivatives in DE-A 198 07 502, morpholine 2,3-dione and its derivatives in WO 03/031482, 2-oxotetrahydro-1,3-oxazine and its derivatives in DE-A 198 54 573, N-acyl-2-oxazolidones in DE-A 198 54 574 and bis- and poly-2-oxazolidinones in DE-A 198 07 992.

Prior German patent application 103 34 584.1 describes the use of bicyclic amide acetals for postcrosslinking.

WO 02/060983 describes superabsorbent particles which are aftertreated with a water-insoluble metal phosphate. In fact, metal phosphate particles are associated with the surface of the superabsorbent particles. This results in superabsorbents of high absorption capacity, improved fluid transportation and high swell rate. The metal phosphate particles preferably have an average particle size in the range from 2 to 7 µm, i.e., attrition of the metal phosphate particles creates an appreciable fraction of fine dust.

Prior German patent application 10 2004 015 686.7 discloses the production of finely divided hydrogels of high permeability. Calcium phosphate particles are subsequently applied to the hydrogel and fixed by addition of dendritic polymers.

The present invention accordingly has for its object to provide water-absorbing polymeric particles of high permeability in the swollen state, which do not dust, which do not require any special apparatus to apply the phosphate layer, nor are in need of costly auxiliary materials.

We have found that this object is achieved by adding water-insoluble metal sulfates, especially calcium sulfate, into the monomer solution before the polymerization or by admixing into the reaction mass during the reaction. The addition can be effected not only as powder metering in a suitable mixing element or preferably as an aqueous dispersion of the sulfate. Instead of pure sulfates, it is also possible to use their hydrates or any desired mixtures of these components. The present invention provides that only sufficient sulfate is added to achieve a distinct increase in saline flow conductivity but the absorption capacity of the superabsorbent is not significantly reduced. If too much sulfate is added, the water-absorbing polymer is unnecessarily diluted and hence the absorption capacity lowered, which is normally not desired.

Water-insoluble refers to a solubility of less than 2 g, preferably of less than 0.1 g and more preferably of less than 0.01 g in 100 ml of water at 25° C.

The water-absorbing polymers thus produced have higher centrifuge retention capacity (CRC) values, higher absorbency under load (AUL 0.7 psi) values and especially higher saline flow conductivity (SFC) values than the otherwise identical comparative polymer without sulfate. We have further found that the requisite residence time of the sulfated polymers in the postcrosslinking stage is distinctly reduced compared with the otherwise identical comparative polymer.

Consequently, the process of the present invention allows higher throughputs yet provides water-absorbing polymers of improved quality.

The water-absorbing polymers of the present invention can be produced by polymerization of a mixture of
a) at least one ethylenically unsaturated acid-functional monomer which may each be at least partly, for example from 5 to 100 mol %, neutralized,
b) at least one crosslinker,
c) if appropriate one or more ethylenically and/or allylically unsaturated monomers copolymerizable with a), and
d) if appropriate one or more water-soluble polymers which may be at least partially grafted with the monomers a), b) and if appropriate c),
the resulting base polymer A being if appropriate postneutralized, so that in total from 25 to 100 mol % and preferably from 65 to 90 mol % of the acid groups are neutralized, dried, classified and aftertreated with
e) at least one postcrosslinker.

The water-insoluble metal sulfate can be added to the monomer solution in bulk as a powder or as an aqueous dispersion prior to polymerization, i.e., before initiating free radicals are deliberately generated in the monomer solution, or during polymerization, i.e., at a monomer conversion of not more than 90%, preferably not more than 70% and more preferably not more than 50%.

When an aqueous dispersion is used, the concentration of metal sulfate in the dispersion is typically in the range from 1% to 70% by weight, preferably in the range from 5% to 60% by weight, more preferably in the range from 10% to 50% by weight and most preferably in the range from 20% to 40% by weight.

Preferably, the insoluble metal sulfate is added in the vicinity of the peak maximum temperature. For batch processes this means that the addition takes place typically not more than 15 minutes, preferably not more than 10 minutes and more preferably not more than 5 minutes before or after the time at which the polymerization temperature reaches its maximum. For continuous processes, the same applies, i.e., the addition takes place typically not more than 15 residence time minutes, preferably not more than 10 residence time minutes and more preferably not more than 5 residence time minutes upstream or downstream of the point at which the polymerization temperature reaches its maximum.

The insoluble metal sulfate, preferably calcium sulfate, is typically rated such that its amount based on the water-absorbing polymer is less than 5% by weight, preferably less than 3% by weight, more preferably less than 1.5% by weight and most preferably in the range from 0.001% to 0.75% by weight.

The process of the present invention can also utilize the known hydrates of calcium sulfate and also further water-insoluble sulfates, an example being barium sulfate.

Similarly to the water-insoluble sulfates, one or more water-insoluble phosphates, for example calcium phosphate, can also be used. Water-insoluble phosphates likewise increase saline flow conductivity (SFC). It is further possible to use one or more sulfates together with one or more phosphates.

The hydrophilic, highly swellable hydrogels (base polymer A) producible in the process of the present invention are in particular polymers of crosslinked (co)polymerized hydrophilic monomers, polyaspartic acid, graft (co)polymers of one or more hydrophilic monomers on a suitable grafting base, crosslinked cellulose ethers, crosslinked starch ethers or natural products which are swellable in aqueous fluids, such as guar derivatives for example. Preferably the polymer to be crosslinked is a polymer which comprises structural units which are derived from acrylic acid or acrylic esters or which were obtained by graft copolymerization of acrylic acid or acrylic esters onto a water-soluble polymeric matrix. These hydrogels are known to one skilled in the art and are described for example in U.S. Pat. No. 4,286,082, DE-C 27 06 135, U.S. Pat. No. 4,340,706, DE-C 37 13 601, DE-C 28 40 010, DE-A 43 44 548, DE-A 40 20 780, DE-A 40 15 085, DE-A 39 17 846, DE-A 38 07 289, DE-A 35 33 337, DE-A 35 03 458, DE-A 42 44 548, DE-A 42 19 607, DE-A 40 21 847, DE-A 38 31 261, DE-A 35 11 086, DE-A 31 18 172, DE-A 30 28 043, DE-A 44 18 881, EP-A 801 483, EP-A 455 985, EP-A 467 073, EP-A 312 952, EP-A 205 874, EP-A 499 774, DE-A 26 12 846, DE-A 40 20 780, EP-A 205 674, U.S. Pat. No. 5,145,906, EP-A 530 438, EP-A 670 073, U.S. Pat. No. 4,057,521, U.S. Pat. No. 4,062,817, U.S. Pat. No. 4,525,527, U.S. Pat. No. 4,295,987, U.S. Pat. No. 5,011,892, U.S. Pat. No. 4,076,663 or U.S. Pat. No. 4,931,497.

Examples of hydrophilic monomers useful for preparing these swellable hydrogel-forming polymers are polymerization-capable acids, such as acrylic acid, methacrylic acid, vinylsulfonic acid, vinylphosphonic acid, maleic acid including its anhydride, fumaric acid, itaconic acid, 2-acrylamido-2-methylpropanesulfonic acid, 2-acrylamido-2-methylpropanephosphonic acid and also their amides, hydroxyalkyl esters and amino- or ammonio-containing esters and amides and also the alkali metal and/or ammonium salts of the acid-functional monomers. Also suitable are water-soluble N-vinylamides such as N-vinylformamide or else diallyldimethylammonium chloride. Preferred hydrophilic monomers are compounds of the general formula I

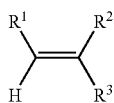

(I)

where
$R^1$ is hydrogen, $C_1$-$C_4$-alkyl, e.g., methyl or ethyl, or carboxyl,
$R^2$ is —$COOR^4$, hydroxysulfonyl or phosphonyl, a $C_1$-$C_4$-alkanol-esterified phosphonyl group or a group of the formula II

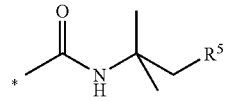

(II)

$R^3$ is hydrogen, $C_1$-$C_4$-alkyl, for example methyl or ethyl,
$R^4$ is hydrogen, $C_1$-$C_4$-aminoalkyl, $C_1$-$C_4$-hydroxyalkyl, alkali metal ion or ammonium ion, and
$R^5$ is a sulfonyl group, a phosphonyl group or a carboxyl group or an alkali metal or ammonium salt of each of these.

Examples of $C_1$-$C_4$-alkanols are methanol, ethanol, n-propanol, isopropanol or n-butanol.

Particularly preferred hydrophilic monomers are acrylic acid and methacrylic acid and also their alkali metal or ammonium salts, for example sodium acrylate, potassium acrylate or ammonium acrylate.

Suitable grafting bases for hydrophilic hydrogels obtainable via graft copolymerization of olefinically unsaturated acids or their alkali metal or ammonium salts may be of natural or synthetic origin. Examples are starch, cellulose or cellulose derivatives and also other polysaccharides and oligosaccharides, polyalkylene oxides, in particular polyethylene oxides and polypropylene oxides, and also hydrophilic polyesters.

Suitable polyalkylene oxides have for example the formula III

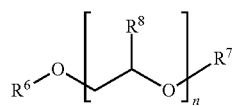

(III)

where
$R^6$ and $R^7$ are each independently hydrogen, $C_1$-$C_{12}$-alkyl, for example methyl, ethyl, n-propyl or isopropyl, $C_2$-$C_{12}$-alkenyl, for example ethenyl, n-propenyl or isopropenyl, $C_7$-$C_{20}$-aralkyl, for example phenylmethyl, 1-phenylethyl or 2-phenylethyl, or aryl, for example 2-methylphenyl, 4-methylphenyl or 4-ethylphenyl,
$R^8$ is hydrogen or methyl, and
n is an integer from 3 to 10 000.
$R^6$ and $R^7$ are each preferably hydrogen, $C_1$-$C_4$-alkyl, $C_2$-$C_6$-alkenyl or phenyl.

Preferred hydrogels are in particular polyacrylates, polymethacrylates and also the graft polymers described in U.S. Pat. No. 4,931,497, U.S. Pat. No. 5,011,892 and U.S. Pat. No. 5,041,496.

The swellable hydrogel-forming polymers are preferably in crosslinked form; that is, they comprise compounds having at least two double bonds which have been interpolymerized into the polymer network. Suitable crosslinkers are in particular N,N'-methylenebisacrylamide and N,N'-methylenebismethacrylamide, esters of unsaturated mono- or polycarboxylic acids of polyols, such as diacrylate or triacrylate, examples being the diacrylates and dimethacrylates of butanediol and ethylene glycol and also trimethylolpropane triacrylate and allyl compounds such as allyl (meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP-A-0 343 427. Particularly suitable crosslinkers are di- and triacrylates of multiply ethoxylated glycerol, trimethylolpropane or trimethylolethane and also their corresponding Michael adducts. For example, a diacrylate and a triacrylate may combine during the synthesis to form a pentaacrylate which can be used as a crosslinker alone or in any desired mixtures with the original di- or triacylate. Preference is given to triacrylates of 3- to 20-tuply ethoxylated glycerol or trimethylolpropane.

The process of the present invention may further utilize hydrogels which are prepared using polyallyl ethers as crosslinkers and by acidic homopolymerization of acrylic acid. Suitable crosslinkers are pentaerythritol triallyl ether, pentaerythritol tetraallyl ether, polyethylene glycol diallyl ether, ethylene glycol diallyl ether, glycerol diallyl ether, glycerol triallyl ether, polyallyl ethers based on sorbitol, and also ethoxylated variants thereof.

The preferred methods of making the base polymer which can be used in the process of the present invention are described in "Modern Superabsorbent Polymer Technology", F. L. Buchholz and A. T. Graham, Wiley-VCH, 1998, pages 77 to 84.

Particular preference is given to base polymers which are produced in a kneader as described for example in WO 01/38402 and WO 02/32964 or on a belt reactor as described for example in EP-A 955 086, EP-A 1097 946 and EP-A 228 638.

The water-absorbing polymer is preferably a polymeric acrylic acid or a polyacrylate. This water-absorbing polymer may be prepared according to a literature method. Preference is given to polymers which comprise crosslinking comonomers in amounts from 0.001 to 10 mol % and preferably from 0.01 to 1 mol %, but most preference is given to polymers which were obtained by free-radical polymerization using a polyfunctional ethylenically unsaturated free-radical crosslinker which additionally bears at least one free hydroxyl group (such as for example pentaerythritol triallyl ether, trimethylolpropane diallyl ether, glyceryl diacrylate).

The swellable hydrogel-forming polymers are preparable by conventional polymerization processes. Preference is given to addition polymerization in aqueous solution by the process known as gel polymerization. In this process from 15 to 50% by weight aqueous solutions of one or more hydrophilic monomers and if appropriate of a suitable grafting base are polymerized in the presence of a free-radical initiator, preferably without mechanical mixing, by utilizing the Trommsdorff-Norrish effect (Makromol. Chem. 1, 169 (1947)). The addition polymerization reaction may be carried out in the temperature range between 0 and 150° C. and preferably between 10 and 100° C., not only at atmospheric pressure but also at elevated or reduced pressure. As customary, the addition polymerization may also be carried out in a protective gas atmosphere, preferably under nitrogen and/or water vapor. The addition polymerization may be initiated using high-energy electromagnetic radiation or the customary chemical addition polymerization initiators, for example organic peroxides, such as benzoyl peroxide, tert-butyl hydroperoxide, methyl ethyl ketone peroxide, cumene hydroperoxide, azo compounds such as azodiisobutyronitrile and also inorganic peroxo compounds such as $(NH_4)_2S_2O_8$, $K_2S_2O_8$ or $H_2O_2$. They may if appropriate be used in combination with reducing agents such as sodium bisulfite and iron(II) sulfate or redox systems where the reducing component is an aliphatic and aromatic sulfinic acid, such as benzenesulfinic acid and toluenesulfinic acid or derivatives thereof, such as Mannich adducts of sulfinic acids, aldehydes and amino compounds as described in DE-A-13 01 566. The performance properties of the polymers may be further improved by postheating the polymer gels for a number of hours in the temperature range from 50 to 130° C. and preferably from 70 to 100° C.

The gels obtained are neutralized, for example to an extent in the range from 25 to 100 mol %, preferably 50 and 90 mol %, especially between 60 and 90 mol %, most preferably between 65 and 80 mol % and between 65 and 72 mol %, based on monomer used, for which the customary neutralizing agents can be used, preferably alkali metal hydroxides or oxides, but very preferably sodium hydroxide, sodium carbonate and sodium bicarbonate. The pH of the neutralized base polymer is typically between 4.5 and 7.5 and preferably between 5.6 and 6.2.

Neutralization is customarily effected by mixing in the neutralizing agent as an aqueous solution or preferably as a solid. Neutralization is preferably effected in the monomer solution, prior to polymerization. But it is also possible to neutralize or postneutralize the polymeric gel. For this purpose the gel is typically mechanically comminuted, by means of a meat grinder for example, and the neutralizing agent is sprayed on, scattered over or poured on and then carefully mixed in. To effect homogenization, the resultant gel mass may be passed through the meat grinder again a number of times.

The neutralized gel mass is dried with a belt dryer or roller dryer until the residual moisture content is preferably less than 15% by weight, more preferably less than 8% by weight and especially less than 5% by weight. The dried base polymer A is then ground and sieved, the customary grinding apparatus being roll mills, pin mills or swing mills. The particle size of the sieved base polymer A is preferably in the range from 45 to 1000 µm, more preferably in the range from 45 to 850 µm, even more preferably in the range from 100 to 800 µm and yet even more preferably in the range from 100 to 700 µm. Further preferred particle sizes are in the range from 100 to 500 µm, from 150 to 600 µm, from 300 to 600 µm, less than 600 µm, less than 400 µm, more preferably less than 300 µm and most preferably less than 150 µm. These ranges include not less than 80% and preferably not less than 90% of all particles.

Suitable base polymers can also be obtained using the further disclosed methods of making in EP-A 316 792, EP-A 400 283, EP-A 343 427, EP-A 205 674 and DE-A 44 18 818. Spray polymerization processes can be used as well.

The base polymers A obtained from continuous kneader and belt polymerization systems are most preferred.

The CRC value [g/g] of base polymer A can be measured by the methods indicated in the description part and is preferably not less than 27, especially not less than 29, more preferably not less than 31 and not more than 45 and preferably not more than 39.

The AUL 0.3 psi value [g/g] of base polymer A can be measured by the methods indicated in the description part and is typically not less than 9, preferably not less than 14, especially not less than 17, more preferably not less than 21 and not more than 27, and preferably not more than 23.

The postcrosslinking of swellable hydrogel-forming polymers is typically carried out by spraying a solution of the surface postcrosslinker onto the dry base polymer powder. After spraying, the polymeric powder is thermally dried, and the crosslinking reaction can take place not only before but also during the drying.

The spraying with a solution of the crosslinker is preferably carried out in reaction mixers or mixing and drying ranges, such as for example Lödige® mixers, BEPEX® mixers, NAUTA® mixers, SCHUGI® mixers, NARA® dryers and PROCESSALL®. Fluidized bed dryers can be used as well.

Drying may take place in the mixer itself, by heating the jacket or introducing a stream of warm air. It is similarly possible to use a downstream dryer, such as for example a tray dryer, a rotary tube oven or a heatable screw. But it is also possible for example to utilize an azeotropic distillation as a drying process.

Preferred drying temperatures are in the range from 50 to 250° C., preferably in the range from 60 to 200° C. and more preferably in the range from 130 to 195° C. The preferred residence time at this temperature in the reaction mixer or dryer is below 60 minutes, preferably below 30 minutes and more preferably below 10 minutes.

The surface postcrosslinkers can be used alone or combined with other surface postcrosslinkers, for example ethylene glycol diglycidyl ether, diethylene glycol diglycidyl ether, polyethylene glycol diglycidyl ether, propylene glycol diglycidyl ether, dipropylene glycol diglycidyl ether, polypropylene glycol diglycidyl ether, glycerol diglycidyl ether, polyglycerol diglycidyl ether, epichlorohydrin, ethylenediamine, ethylene glycol, diethylene glycol, triethylene glycol, polyethylene glycol, propylene glycol, dipropylene glycol, tripropylene glycol, polypropylene glycol, butylene glycol, 1,3-propanediol, 2-methyl-1,3-propanediol, 1,4-butanediol, bisphenol A, glycerol, 1,5-pentanediol, 1,6-hexanediol, neopentylglycol, trimethylolpropane, pentaerythritol, sorbitol, diethanolamine, triethanolamine, ethylenediamine, ethylene carbonate, propylene carbonate, 2-oxazolidones, such as 2-oxazolidinone or N-hydroxyethyl-2-oxazolidinone, 2,3-morpholinediones, such as N-2-hydroxyethyl-2,3-morpholinedione, N-methyl-2,3-morpholinedione, N-ethyl-2,3-morpholinedione and/or N-tert-butyl-2,3-morpholinedione, 2-oxotetrahydro-1,3-oxazine, N-acyl-2-oxazolidones, such as N-acetyl-2-oxazolidone, bicyclic amide acetals, such as 5-methyl-1-aza-4,6-dioxabicyclo[3.3.0]octane, 1-aza-4,6-dioxabicyclo[3.3.0]octane and/or 5-isopropyl-1-aza-4,6-dioxabicyclo[3.3.0]octane, and/or bis- and poly-2-oxazolidinones.

The surface postcrosslinker is preferably dissolved in solvents which are not self-reactive at a given operating temperature, preferably in lower alcohols, examples being methanol, ethanol, isopropanol, propylene glycol, ethylene glycol, preferably isopropanol, and most preferably in aqueous solutions of such suitable alcohols, in which case the alcohol content of the solution is in the range from 10% to 90% by weight, more preferably between 25% to 70% by weight and especially between 30% to 50% by weight. Any desired mixtures of alcohols can be used as well.

The surface postcrosslinker is used in an amount from 0.01% to 1% by weight, based on the polymer used, and the crosslinker solution itself is used in an amount from 1% to 20% by weight and preferably from 3% to 15% by weight, based on the polymer used.

Preferred postcrosslinkers are 2-oxazolidones; such as 2-oxazolidinone or N-hydroxyethyl-2-oxazolidinone, N-acyl-2-oxazolidones, such as N-acetyl-2-oxazolidone, 2-oxotetrahydro-1,3-oxazine, bicyclic amide acetals, such as 5-methyl-1-aza-4,6-dioxa-bicyclo[3.3.0]octane, 1-aza-4,6-dioxa-bicyclo[3.3.0]octane and/or 5-isopropyl-1-aza-4,6-dioxa-bicyclo[3.3.0]octane, bis-2-oxazolidones and/or poly-2-oxazolidones.

Particularly preferred postcrosslinkers are 2-oxazolidinone, N-hydroxyethyl-2-oxazolidinone or N-hydroxypropyl-2-oxazolidinone.

The present invention further provides water-absorbing polymeric particles comprising
a) at least one interpolymerized ethylenically unsaturated acid-functional monomer whose acid groups may be at least partly, for example from 50 to 85 mol %, neutralized,
b) at least one interpolymerized crosslinker,
c) if appropriate one or more interpolymerized ethylenically and/or allylically unsaturated monomers copolymerizable with a),
d) if appropriate one or more water-soluble polymers which may be at least partially grafted with the monomers a), b) and if appropriate c),
e) at least one converted postcrosslinker, and
f) at least one interpolymerized water-insoluble metal sulfate.

Interpolymerized in connection with the metal sulfate is to be understood as meaning that the metal sulfate is distributed in the polymeric particles. The distribution of the metal phosphate in the polymeric particles is preferably homogeneous or substantially homogeneous. This is in contrast with the processes as described in WO-A-02/60983 for example, in each of which the metal phosphates are sprayed onto the polymeric particles and merely adhere to their surface.

The amount of metal sulfate in the water-absorbing polymer is less than 5% by weight, preferably less than 3% by weight, more preferably less than 1.5% by weight and most preferably in the range from 0.001% to 0.75% by weight. A preferred metal sulfate is calcium sulfate.

A preferred monomer a) is acrylic acid, preferably from 0 to 100 mol %, preferably from 5 to 90 mol %, especially between 25 and 80 mol % and most preferably between 30 and 55 mol % and between 65 and 75 mol %, based on monomer used, neutralized.

The CRC value [g/g] of the postcrosslinked water-absorbing polymers of the present invention can be measured by the methods indicated in the description part and is preferably not less than 20, more preferably not less than 24, even-more preferably not less than 25, yet even more preferably not less than 26 and still more preferably not less than 30.

The AUL-0.7 psi value [g/g] of the postcrosslinked water-absorbing polymers of the present invention can be measured by the methods indicated in the description part and is preferably not less than 15, more preferably not less than 21, even more preferably not less than 22, yet even more preferably not less than 23 and still more preferably not less than 25.

The SFC value [$10^{-7}$ cm$^3$ s/g] of the postcrosslinked water-absorbing polymers of the present invention can be measured by the methods indicated in the description part and is preferably not less than 30, more preferably not less than 45, even more preferably not less than 60, yet even more preferably not less than 70, and still more preferably not less than 80, and not more than 1000.

Particle size ranges which are preferred according to the present invention extend from 50 to 700 μm, preferably from 50 to 500 μm or from 150 to 700 μm, more preferably from 50 to 400 μm or from 150 to 600 μm, and most preferably from 50 to 300 μm or from 150 to 500 μm. These ranges cover not less than 80% by weight, preferably not less than 90% by weight and most preferably up to 100% by weight of all particles.

The present invention further provides for the use of metal sulfates, especially calcium sulfate, in the production of water-absorbing polymers before or during polymerization.

The present invention further provides hygiene articles, such as diapers, tampons or sanitary napkins, especially diapers, comprising a water-absorbing polymer according to the present invention.

To ascertain the quality of postcrosslinking, the dried hydrogel is tested using the test methods described hereinbelow:

Methods:

Unless otherwise stated, the measurements should be carried out at an ambient temperature of 23±2° C. and a relative humidity of 50±10%. The swellable hydrogel-forming polymer is thoroughly mixed through prior to measurement.

Centrifuge Retention Capacity (CRC)

This method measures the free swellability of the hydrogel in a teabag. 0.2000±0.0050 g of dried hydrogel (particle fraction 106-850 μm) is weighed in a teabag 60×85 mm in size, which is subsequently sealed. The teabag is placed for 30 minutes in an excess of 0.9% by weight sodium chloride solution (at least 0.83 l of sodium chloride solution/1 g of polymer powder). The teabag is subsequently centrifuged at 250 G for 3 minutes. The amount of liquid retained by the hydrogel is determined by weighing back the centrifuged teabag.

Centrifuge retention capacity can also be determined by the centrifuge retention capacity test method No. 441.2-02 recommended by EDANA (European Disposables and Nonwovens Association).

Absorbency Under Load (AUL) 0.7 psi (4830 Pa)

The measuring cell for determining the AUL 0.7 psi value is a Plexiglas cylinder 60 mm in internal diameter and 50 mm in height. Adhesively attached to its underside is a stainless steel sieve bottom having a mesh size of 36 μm. The measuring cell further includes a plastic plate having a diameter of 59 mm and a weight which can be placed in the measuring cell together with the plastic plate. The plastic plate and the weight together weigh 1344 g. AUL 0.7 psi is determined by determining the weight of the empty Plexiglas cylinder and of the plastic plate and recording it as $W_0$. Then 0.900±0.005 g of swellable hydrogel-forming polymer (particle size distribution 150-800 μm) is weighed into the Plexiglas cylinder and distributed very uniformly over the stainless steel sieve bottom. The plastic plate is then carefully placed in the Plexiglas cylinder, the entire unit is weighed and the weight is recorded as $W_a$. The weight is then placed on the plastic plate in the Plexiglas cylinder. A ceramic filter plate 120 mm in diameter and 10 mm in height and 0 in porosity is then placed in the middle of a Petri dish 200 mm in diameter and 30 mm in height and sufficient 0.9% by weight sodium chloride solution is introduced for the surface of the liquid to be level with the filter plate surface without the surface of the filter plate being wetted. A round filter paper 90 mm in diameter and <20 μm in pore size (S&S 589 Schwarzband from Schleicher & Schüll) is subsequently placed on the ceramic plate.

The Plexiglas cylinder holding swellable hydrogel-forming polymer is then placed with plastic plate and weight on top of the filter paper and left there for 60 minutes. At the end of this period, the complete unit is taken out of the Petri dish from the filter paper and then the weight is removed from the Plexiglas cylinder. The Plexiglas cylinder holding swollen hydrogel is weighed out together with the plastic plate and the weight is recorded as $W_b$.

Absorbency under load (AUL) is calculated as follows:

$$AUL\ 0.7\ psi\ [g/g]=[W_b-W_a]/[W_a-W_0]$$

Absorbency under load can also be determined by the absorption under pressure test method No. 442.2-02 recommended by EDANA (European Disposables and Nonwovens Association).

Absorbency Under Load (AUL) 0.3 psi (2070 Pa)

The measurement is carried out similarly to AUL 0.7 psi. The weight of the plastic plate and the weight are together 576 g.

Saline Flow Conductivity (SFC)

The saline flow conductivity of a swollen gel layer under a confining pressure of 0.3 psi (2070 Pa) is determined as described in EP-A-0 640 330 as the gel layer permeability of a swollen gel layer of superabsorbent polymer, although the apparatus described on page 19 and in FIG. 8 of the previously cited patent application was modified to the effect that the glass frit (40) is no longer used, the piston (39) is made of the same plastic material as the cylinder (37) and now comprises 21 equally sized holes uniformly distributed over the entire contact surface. The procedure and also evaluation of the measurement remains unchanged compared with EP-A-0 640 330. The flow rate is recorded automatically.

The saline flow conductivity (SFC) is calculated as follows:

$$SFC\ [cm^3s/g]=(F_g(t=0)\times L_0)/(d\times A\times WP),$$

where $F_g(t=0)$ is the flow rate of NaCl solution in g/s obtained from a linear regression analysis of the $F_g(t)$ data of the flow rate determinations by extrapolation to t=0; $L_0$ is the thickness of the gel layer in cm; d is the density of the NaCl solution in $g/cm^3$; A is the area of the gel layer in $cm^2$; and WP is the hydrostatic pressure above the gel layer in $dyn/cm^2$.

EXAMPLES

Example 1

A Lödige VT 5R-MK plowshare kneader 5 l in capacity was charged with 416 g of water, 189.5 g of acrylic acid, 1990.2 g of a 37.3% by weight sodium acrylate solution (100 mol % neutralized) and also 4.55 g (=0.60% by weight based on acrylic acid monomer) of trimethylolpropane-15 EO-triacrylate crosslinker. The initial charge was inertized by bubbling nitrogen through it for 20 minutes. This was followed by initiation through addition of (dilute aqueous solutions) of 2.123 g of sodium persulfate, 0.045 g of ascorbic acid and also 0.126 g of hydrogen peroxide at about 23° C. After initiation, the temperature of the heating jacket was closed loop controlled to the reaction temperature in the reactor. The polymerization was carried out by stirring and thorough mixing through in the kneader. The crumbly gel eventually obtained was then dried at 180° C. in a circulating air cabinet for about 3 hours. This was followed by grinding and classifying to 200-850 μm by sieving off over- and undersize.

The batch was repeated more than once and the powders obtained from the individual batches were mixed and homogenized.

The resulting base polymer A was finally characterized.

The properties of the base polymer A (200 to 850 μm) were as follows:

CRC=35.6 g/g
AUL 0.3 psi=14.3 g/g

Particle size distribution of base polymer A
>850 μm=12.75% by weight
600-850 μm=51.85% by weight
300-600 μm=30.46% by weight
<300 μm=4.95% by weight 1000 g of base polymer A were sprayed with 2.898% by weight of 30.8:69.2 (w/w) isopropanol/water and 0.085% by weight of 2-oxazolidinone (25% by weight solution in 2:1 water/propylene glycol), all based on base polymer, in a solution in one Lödige laboratory mixer, transferred to a second, already preheated Lödige laboratory mixer and postcrosslinked for 120 minutes at a product temperature of 175° C. The polymer obtained was then sieved off at 850 μm to remove any lumps.

The postcrosslinking solution had the following composition: 0.85 g of 2-oxazolidone, 0.85 g of propylene glycol, 8.88 g of isopropanol and 21.8 g of water.

The postcrosslinked, water-absorbing polymer had the following properties:

Particle size distribution after 120 minutes
>850 μm=0.96% by weight
600-850 μm=36.16% by weight
300-600 μm=51.39% by weight
<300 μm=11.49% by weight Examples 2 to 4

Example 1 was repeated to produce a base polymer by adding the amount of calcium phosphate (from Rhodia, type TCP 130) reported in the table which follows, based on monomer reckoned as acrylic acid, as a 30% by weight aqueous suspension to the polymerization shortly before attainment of the peak temperature.

The base polymer was classified to 200-850 μm and postcrosslinked.

For postcrosslinking, 20 g of the base polymer were sprayed with postcrosslinker solution comprising 0.10% by weight of 2-oxazolidone, 1.05% by weight of isopropanol, 245% by weight of water and 20 ppm of Emulsogen V4345, all based on base polymer used, in a Waring laboratory mixer with stirring and then dried at 175° C. in a circulating air cabinet for 60 minutes. This was followed by sieving off at 850 μm to remove lumps.

The properties of base polymer and postcrosslinked polymer are as follows:

| Example | Calcium phosphate | CRC* [g/g] | AUL0.3 psi* [g/g] | CRC** [g/g] | AUL0.7 psi** [g/g] | SFC** [$10^{-7}$ cm$^3$ s g$^{-1}$] |
|---|---|---|---|---|---|---|
| 2 | 0.5% by weight | 32.6 | 19.1 | 32.5 | 24.2 | 50 |
| 3 | 3.0% by weight | 31.0 | 22.4 | 31.2 | 23.0 | 82 |
| 4 | 5.0% by weight | 29.6 | 22.0 | 29.4 | 22.8 | 90 |

*base polymer
**postcrosslinked polymer

| Heat treatment | CRC [g/g] | AUL 0.7 psi [g/g] | SFC [$10^{-7}$ cm$^3$ s g$^{-1}$] |
|---|---|---|---|
| 70 minutes | 30.1 | 24.0 | 26 |
| 120 minutes | 28.9 | 21.7 | 46 |

Examples 5 to 7

Examples 2 to 4 were repeated except that calcium sulfate dihydrate (from Merck, not less than 99% pure) was added instead of calcium phosphate.

The properties of base polymer and postcrosslinked polymer are as follows:

| Example | Calcium sulfate dihydrate | CRC* [g/g] | AUL0.3 psi* [g/g] | CRC** [g/g] | AUL0.7 psi** [g/g] | SFC** [$10^{-7}$ cm$^3$ s g$^{-1}$] |
|---|---|---|---|---|---|---|
| 5 | 0.5% by weight | 32.1 | 23.4 | 32.2 | 24.3 | 80 |
| 6 | 3.0% by weight | 31.0 | 22.3 | 31.2 | 23.2 | 57 |
| 7 | 5.0% by weight | 30.1 | 21.3 | 31.0 | 22.0 | 37 |

*base polymer
**postcrosslinked polymer

We claim:

1. A process for producing water-absorbing polymers by polymerization of a mixture of
   a) at least one ethylenically unsaturated acid-functional monomer, each optionally at least partly neutralized,
   b) at least one crosslinker,
   c) optionally one or more ethylenically and/or allylically unsaturated monomer copolymerizable with a), and
   d) optionally one or more water-soluble polymer, optionally at least partially grafted with the monomers a), b), and c), the resulting base polymer A being aftertreated with
   e) at least one postcrosslinker, the process comprising adding to said mixture, before or during polymerization, at least one water-insoluble metal sulfate in an amount of from 0.001% to 3% by weight based on the water-absorbing polymer produced.

2. The process according to claim 1 wherein the metal sulfate is metered as a powder.

3. The process according to claim 1 wherein the metal sulfate is metered as an aqueous dispersion.

4. The process according to claim 3 wherein the concentration of metal sulfate in the dispersion is in the range from 1% to 70% by weight.

5. The process according to claim 1 wherein the metal sulfate is calcium sulfate.

6. The process according to claim 1 wherein the monomer a) is a partially neutralized acrylic acid.

7. Water-absorbing polymeric particles comprising
   a) at least one interpolymerized ethylenically unsaturated acid-functional monomer each optionally at least partly neutralized,
   b) at least one interpolymerized crosslinker,
   c) optionally one or more interpolymerized ethylenically and/or allylically unsaturated monomer copolymerizable with a),
   d) optionally one or more water-soluble polymer, optionally at least partially grafted with the monomers a), b), and c),
   e) at least one converted postcrosslinker, and
   f) at least one interpolymerized water-insoluble metal sulfate in an amount from 0.001% to 3%, by weight, based on the water-absorbing polymeric particles, the at least one interpolymerized water-insoluble metal sulfate being distributed in the polymeric particles.

8. The water-absorbing polymeric particles according to claim 7 wherein the at least one interpolymerized water-insoluble metal sulfate is calcium sulfate.

9. The water-absorbing polymeric particles according to claim 7 wherein the interpolymerized monomer a) is a partially neutralized acrylic acid.

10. The water-absorbing polymeric particles according to claim 7 wherein the polymeric particles have a saline flow conductivity of not less than $30 \times 10^{-7}$ cm$^3$ s/g.

11. The water-absorbing polymeric particles according to claim 7 wherein the polymeric particles have a saline flow conductivity of not less than $60 \times 10^{-7}$ cm$^3$ s/g.

12. The water-absorbing polymeric particles according to claim 7 wherein the water-absorbing polymeric particles have a centrifuge retention capacity of not less than 24 g/g.

13. Hygiene articles comprising water-absorbing polymeric particles according to claim 7.

* * * * *